United States Patent [19]

Sugisaki et al.

[11] 4,038,087

[45] July 26, 1977

[54] VARNISH FOR PRINTING INKS AND ITS METHOD OF PREPARATION

[75] Inventors: Hiroyuki Sugisaki, Tokyo; Mitsuo Nozue, Kuwana; Hiroki Ogawa, Tokyo, all of Japan

[73] Assignees: Taniguchi Petroleum Refining Company, Limited; T. S. Chemical, Ltd., Tokyo, both of Japan

[21] Appl. No.: 630,683

[22] Filed: Nov. 10, 1975

[30] Foreign Application Priority Data

Mar. 3, 1975    Japan .................................. 50-25835

[51] Int. Cl.$^2$ .................... C07C 139/06; C09D 11/02; C09D 11/12
[52] U.S. Cl. ...................................... 106/32; 106/285; 106/311; 260/125; 260/504 S
[58] Field of Search .......................... 106/32, 311, 285; 208/276, 13, 14; 260/448, 125, 504 A, 504 S; 252/33, 36

[56] References Cited

U.S. PATENT DOCUMENTS

| | | | |
|---|---|---|---|
| 999,611 | 8/1911 | Walker et al. | 260/504 S |
| 2,491,043 | 12/1949 | Hersberger | 260/448 R |
| 2,967,782 | 1/1961 | Manley | 106/32 |
| 2,980,545 | 4/1961 | Shoemaker | 106/285 |

*Primary Examiner*—Theodore Morris
*Attorney, Agent, or Firm*—Oblon, Fisher, Spivak, McClelland & Maier

[57] ABSTRACT

A printing ink varnish which comprises a mineral oil and a product prepared by adding an anionic surfactant to an acid sludge followed by neutralization with an aqueous solution of an alkali metal salt and then adding an inorganic polyvalent metal salt to the mixture to form polyvalent metal salts of the anionic surfactant and acid components of said sludge. A process for preparing the varnish is also disclosed.

17 Claims, No Drawings

VARNISH FOR PRINTING INKS AND ITS METHOD OF PREPARATION

BACKGROUND OF THE INVENTION

1. Field of the Invention

The present invention relates to a process for prearing a varnish for a printing ink using an acid sludge which previously was a source of pollution of the raw material.

2. Description of the Prior Art

Two processes for the preparation of mineral lubricating oils from crude oil are known. One is a hydrogenation-furfural extraction process and the other is a sulfuric acid treatment. In the sulfuric acid treatment, it is possible to prepare lubricating oils having high stability by sulfonation, sulfation, or dissolution in sulfuric acid and an extraction of unsaturated hydrocarbons, resinous matter, asphalts and amines which are in petroleum fractions. The by-product of the sulfuric acid treatment is referred as an acid sludge, has strong acidity and contains relatively large amounts of oil components. As a result, it is difficult to effectively utilize this sludge and it is also difficult to dispose of. Typically, the acid sludge is disposed of by neutralization with limestone or by burning.

SUMMARY OF THE INVENTION

It is an object of the present invention to prepare a varnish for printing inks by utilizing the acid sludge which previously has been difficult to dispose of. It is another object of the invention to provide a varnish for a printing ink which is low in cost and imparts excellent printing characteristics.

The objects of the present invention have been achieved by preparing a varnish which comprises a mineral oil and a product prepared by adding an anionic surfactant to the acid sludge by-product in the preparation of a mineral lubricating oil from crude oil, neutralizing the acid sludge with an aqueous alkali solution and, then, adding an inorganic polyvalent metal salt to the mixture to form polyvalent metal salts of the anionic surfactant and acid components of the acid sludge.

DETAILED DESCRIPTION OF THE PREFERRED EMBODIMENTS

The anionic surfactants suitable for use in this invention include fatty acid type surfactants, naphthenic acid type surfactants, sulfonic acid type surfactants and sulfate type surfactants, all of which are well known in the art. The acid sludge may be washed with water, if desired. The anionic surfactant is admixed with the acid sludge and then the mixture is neutralized with an aqueous solution of an alkali metal salt such as sodium hydroxide, sodium carbonate and the like, whereby alkali salts such as sodium salts of acid components of the acid sludge and the anionic surfactant are formed. It is possible, however, to add the anionic surfactant after first washing the acid sludge with an aqueous alkai solution to neutralize the sludge. It is also possible to add a mixture of the anionic surfactant and the aqueous solution of alkali to the acid sludge. When the anionic surfactant is acidic when it is mixed with the acid sludge, an excellent emulsion, which is advantageous, may be formed by adding the aqueous alkali solution to the mixture.

the alkali metal salts, such as the sodium salt, of the surfactant and the acid components of the acid sludge are converted to the polyvalent metale salts thereof, by adding an inorganic polyvalent metal salt to the mixture.

In the sulfuric acid treatment of petroleum fractions, a large amount of resinous matter is formed as an acid sludge by the action of the concentrated sulfuric acid. Typical acid sludges include transformer oil sludge, spindle oil sludge, machine oil sludge, motor oil sludge, and the like. These acid sludges are uniform liquids containing resinous matter and sulfuric acid. The viscosities of the acid sludges increase with the increased ratio of resinous matter contained in the sludge. The viscosity of the sludges increase from the transformer oil sludge, to the spindle oil sludge, the machine oil sludge and to the motor oil sludge which is the most viscous. The acid sludges should be treated depending upon the ratio of the resinous matter.

One embodiment using an acid sludge having high ratio of the resinous matter such as machine oil sludge and motor oil sludge will be illustrated first.

The anionic surfactants used in the invention can be by-products formed in the oil and fat industry or petroleum refining industry. Typical surfactants are fatty acid-type surfactants, fatty acid pitch-type surfactants, naphthenic acid-type surfactants, sulfonic acid-type surfactants and sulfate-type surfactants. Suitable surfactants also include resin acid pitches as a waste prepared in the production of fatty acids and fatty acids glycerides, and glycerine, and naphthenic acids prepared in the petroleum refining process; and organic sulfonic acids and sulfates prepared in sulfuric acid treatments. These anionic surfactants may be incorporated in an acidic condition.

When alkali slats of the anionic surfactants are admixed with the acid sludge, these surfactants are converted to acid-type surfactants during the mixing with the acid sludge.

A uniform alkali emulsion is formed when the acid sludge in which the acid type surfactant has been uniformly mixed, is mixed with an aqueous solution of an alkali, such as sodium hydroxide, sodium carbonate and the like, and the mixture is heated with stirring. As a result of the addition of the alkali, the acid components of the surfactant and the acid sludge are neutralized to form alkali metal salts such as sodium salts thereof. Next, an inorganic polyvalent metal salt such as calcium chloride, magnesium chloride, aluminum sulfate and the like, preferably the aluminum salt, is added to the reaction mixture to adjust pH to about 3-7 whereby the alkali salts of the acid sludge, the fatty acids and the fatty acid pitches, the naphthenic acids, the organic sulfonic acids and the organic sulfates are converted to the corresponding polyvalent metal salt such as the aluminum salt, calcium salt, magnesium salt, etc. The reactions for forming the aluminum salt of the surfactants are typical and are as follows:

wherein R represents an alkyl group and RSO₃Na represents sodium salts of the acid sludge and the organic sulfonic acd; RCOONa represents sodium salts of the surfactant such as the fatty acids, the fatty acid pitches, and the naphthenic acids. The calcium, magnesium and aluminum salts of these anionic surfactants are a pale yellow-black, brown color, semi-fluids, and separate into a layer which floats on the water. After removing the water layer, it is desirable to add an aqueous solution of sodium hydroxide to the product to adjust the pH to 7-11. The mixture is then heated to evaporate water. Next, a mineral oil is dispersed in the resulting resinous matter with stirring whereby a varnish for a printing ink is obtained. Mineral oils used in this invention may include petroleum type solvents, (boiling points of 450°-600° F); spindle oils, machine oils, motor oils, cylinder oils, or the like.

A characteristic feature of this invention is to disperse the resinous matter in the mineral oil under high shearing force. The high shearing force is applied by using a dispersing mixer having a high speed rotary disc, a three roll mill, a pearl mill or the like.

The transformer oil sludge and the spindle oil sludge have a relatively lower ratio of the resinous matter, a higher sulfuric acid content and a lower viscosity than machine oil sludge and motor oil sludge. When using transformer oil sludge or spindle oil sludge, the sludge is heated at 50°-150° C for 1-48 hours. This heating forms a polymerized sludge having a higher viscosity and a higher resinous content than the starting sludge. The sludge separates as the upper phase and an aqueous solution of sulfuric acid separates as the lower phase. This polymerized sludge may then be used instead of the machine oil sludge or motor oil sludge in the procedure previously described for preparing the varnish for a printing ink.

Alternatively, when transformer oil sludge or spindle oil sludge is used, carbon black or oil carbon (by-product carbon produced by Texaco method) is added to the sludge and the mixture is stirred in a kneader whereby the resinous matter in the acid sludge is combined with the carbon black and an aqueous solution of sulfuric acid separates a separate layer. This mixture of the resinous matter and carbon black is used instead of the machine oil sludge or the motor oil sludge in the procedure described above, whereby a varnish for a printing ink containing carbon black may be prepared. In one embodiment, a surface treatment of the carbon black is performed with the sulfuric acid in the acid sludge whereby carbon black which has a higher affinity for mineral oil and which imparts a higher degree of color is obtained. The varnish which contains crystalline sodium sulfate, as an impurity is purified by a centrifugal separation, canvas filteration or the like.

Generally, the anionic surfactant, such as as the fatty acid-type surfactants, the fatty acid pitch-type surfactants, the napthenic acid-type surfactants, the sulfonic acid-type surfactants and the sulfate type-surfactants, are added directly to the acid sludge. However, it is possible to add the surfactant after washing the acid sludge with water and it is also possible to add the surfactant with an alkali or after neutralization of the sludge with an alkali. However, it is necessary to mix the surfactant with the resinous matter in the acid sludge with a high degree of mixing.

The amount of the surfactant added to the acid sludge is about 5-150 wt. %, preferably 10-80 wt. % of the resinous matter in the acid sludge.

The amount of the alkali such as sodium hydroxide or sodium carbonate added is at least sufficient to neutrlize the acid components of the acid sludge and the surfactants. An excess may be added.

The amount of the inorganic polyvalent metal salt such as aluminum, calcium and magnesium salts added is at least sufficient to convert all of the alkali salts, such as sodium salts to polyvalent metal salts. An excess of polyvalent metal may be added. The resinous matter converted to the polyvalent metal salts, such as aluminum, calcium and magnesium salts, is dispersed in a mineral oil at the desired ratio. If desired, other resins may be added to prepare the varnish for the printing ink. The other resins, the mineral oils added and other additives are all known components of conventional varnishes for a printing ink, and may be selected as desired.

Resinous matter prepared from acid sludge pitch (polymerized acid sludge) can be incorporated at a rate of 5-100 wt. %, preferably 20-100 wt. % of the total resinous matter in the varnish for printing inks.

In accordance with this invention, acid sludge which previously had no utility and was difficult to dispose of, may be used as the raw material to prepare varnishes for printing inks.

Accordingly, the treatment of the acid sludge by the method of this invention is remarkably advantageous from the viewpoint of the inhibition of the pollution and the effective utilization of petroleum sources.

Having generally described the invention, a more complete understanding can be obtained by reference to certain specific examples, which are included for purposes of illustration only and are not intended to be limiting unless otherwise specified.

EXAMPLE 1

Preparation of a Varnish for a Rotary Printing Press Ink

A mixture of 100 wt. parts of machine oil sludge and 20 wt. parts of fatty acid pitch (total acid vlaue of 30; saponification value of 120) was neutrlaized by adding dropwise while stirring 50 wt. parts of a 50% aqueous solution of sodium hydroxide. The amount of the aqueous solution of sodium hydroxide added was controlled depending upon the total acid value so as to adjust the pH to 11. The neutralization reaction is exothermic and the temperature of the reaction mixture rises about 100° C. Accordingly, 300 wt. parts of water was gradually added to lower the temperature of the reaction mixture. The resulting aqueous alkali solution was mixed with 40 wt. parts of a 50% aqueous solution of aluminum sulfate by stirring; the pH of the resulting mixture was 4. The aluminum slats of the acidic componenets of the machine oil sludge and the fatty acid pitch were flocculated and floated on the water phase. After removing the water, 4 wt. parts of a 50% aqueous solution of sodium hydroxide was added to the resinous matter to adjust the pH to 7. The mixture was heated at 100°-120° C to evaporate water which remained in the aluminum salts of the acidic components. Then 120 wt. parts of a machine oil were added and the aluminum salts of the acidic component were dispersed and dissolved in the machine oil with vigorous stirring. The impurities such as crystalline sodium sulfate were separated by a centrifugal separator to obtain the varnish for a rotary printing press ink.

EXAMPLE 2

Preparation of a Varnish for a Newspaper Ink

A mixture of 30 wt. parts of a machine oil sludge and 21 wt. parts of a fatty acid pitch (total acid value of 30 and saponification value of 120) was neutralized by adding dropwise while stirring, 15 wt. parts of 50% aqueous solution of sodium hydroxide to adjust the pH to 11. Then 80 wt. parts of water was added to the reaction mixture to form a uniform aqueous alkali solution. The resulting aqueous alkali solution was mixed with 15 wt. part of a 50% aqueous solution of aluminum sulfate by stirring; the pH of the resulting mixture was 4. The aluminum salts of the acidic components of the machine oil sludge and the fatty acid pitch were flocculated and floated on the water phase. After removing the water, 3 wt. parts of a 50% aqueous solution of sodium hydroxide was added to the resinous matter to adjust the pH to 9. Then, 513 wt parts of a machine oil were added and the aluminum salts of the acidic components were dispersed and dissolved in the machine oil with vigorous stirring. The impurities, such as crystalline sodium sulfate were separated by a centrifugal separator to obtain the varnish suitable for a newspaper ink. In the preparation of newspaper ink, the resinous matter dissolved in the varnish should not precipitate when a light mineral oil is added as the solvent. The varnish for the ink was admixed with from 10–100 times of a light mineral oil, no precipitation of the resinous matter occurred.

EXAMPLE 3

Preparation of Varnish for Newspaper Ink

A mixture of 100 wt. parts of a motor oil sludge, 20 wt. parts of a fatty acid (total acid value of 160) and 20 wt. parts of a naphthenic acid (total acid value of 150) was neutralized with 60 wt. parts of a 50% aqueous solution of sodium hydroxide to adjust the pH to 11. Next, 300 wt. parts of water was added to the reaction mixture to form an uniform aqueous alkali solution. The resulting aqueous alkali solution was mixed with 40 wt. parts of a 50% aqueous solution of aluminum sulfate with stirring; the pH of the resulting mixture was 4. the alumnium salts of the acidic components of the motor oil sludge, the fatty acid and the naphthenic acid were flocculated and floated on the water phase. After removing the water, 6 wt. parts of a 50% aqueous solution of sodium hydroxide was added to the resinous matter to adjust the pH to 8. The product was then heated to 100–120° C to evaporate the remainin water. Then, 580 wt. parts of a machine oil were added and the aluminum salts of the acidic components were dispersed and dissolved in the machine oil with vigorous stirring. The impurities, such as crystalline sodium sulfate, were separated by a centrifugal separator to obtain the varnish suitable for a newspaper ink.

EXAMPLE 4

Preparation of a Varnish for a Rotary Printing Press Ink

A mixture of 100 wt. parts of machine oil sludge, 10 wt. parts of fatty acid pitch (total acid value of 30 and saponification value of 120) and 10 wt. parts of naphthenic acid (total acid value of 150) was neutralized with 50 wt. parts of a 50% aqueous solution of sodium hydroxide to adjust the pH to 11. Then, 350 wt. parts of water were added to the reaction mixture to form a uniform aqueous alkali solution. The resulting aqueous alkali solution was mixed with 60 wt. parts of a 35% aqueous solution of calcium chloride and 5 wt. parts of concentrated hydrochloric acid by stirring. The calcium salts of the acidic components of the machine sludge, the fatty acid pitch and the naphthenic acid were flocculated and floated on the water phase. After removing the water, 4 wt. parts of a 50% aqueous solution of sodium hydroxide was added to the resinous matter to adjust the pH to 7. The product was then heated at 100°–120°C to evaporate the remaining water. Next, 120 wt. parts of a machine oil were added and the calcium salts of the acidic components were dispersed and dissolved in the machine oil by vigorous stirring. The impurities, such as crystalline sodium sulfate, were separated by a centrifugal separator, to obtain the varnish for a rotary printing press ink.

Having now fully described the invention, it will be apparent to one of ordinary skill in the art that many changes and modifications can be made thereto without departing from the spirit or scope of the invention as set forth herein.

What is claimed as new and desired to be secured by Letters Patents of the United States is:

1. A varnish for a printing ink which comprises a mineral oil and a product prepared by adding an anionic surfactant to an acid sludge, neutralizing said acid sludge with an aqueous solution of an alkali metal salt and then, adding an inorganic polyvalent metal salt to the mixture to form polyvalent metal salts of said anionic surfactant and acid components of said acid sludge.

2. The varnish for a printing ink of claim 1, wherein said acid sludge is selected from transformer oil sludge, spindle oil sludge, machine oil sludge and motor oil sludge.

3. The varnish for a printing ink of claim 1, wherein said acid sludge is selected from machine oil sludge and motor oil sludge.

4. The varnish for a printing ink of claim 1, wherein said acid sludge is a polymerized sludge of a pitch prepared by heating a transformer oil sludge or a spindle oil sludge.

5. The varnish for a printing ink of claim 1, wherein transformer oil sludge or spindle oil sludge is mixed with carbon black or oil carbon before neutralization.

6. The varnish for a printing ink of claim 1, wherein said anionic surfactant is selected from fatty acid-type surfactants, naphthenic acid-type surfactants, sulfonic acid-type surfactants and sulfate-type surfactants.

7. The varnish for a printing ink of claim 1, wherein said anionic surfactant is added after washing said acid sludge with water.

8. The varnish for a printing ink of claim 1, wherein said polyvalent inorganic salt is a water soluble aluminum salt.

9. The varnish for a printing ink of claim 1, wherein said anionic surfactant is added after washing said acid sludge with water.

10. A method for converting acid sludge into a varnish for printing inks which comprises; mixing an anionic surfactant with the acid sludge; neutralizing the resulting mixture with an alkali metal salt; then adding a sufficient amount of a polyvalent metal salt to convert all of the alkali metal salts of the surfactant and sludge to polyvalent metal salts, recovering the product so formed and mixing it with a mineral oil.

11. The method of claim 10, wherein said acid sludge is selected from transformer oil sludge, spindle oil sludge, machine oil sludge and motor oil sludge.

12. The method of claim 10, wherein said acid sludge is selected from machine oil sludge and motor oil sludge.

13. The method of claim 10, wherein said acid sludge is a polymerized sludge of a pitch prepared by heating a transformer oil sludge or a spindle oil sludge.

14. The method of claim 10, wherein transformer oil sludge or spindle oil sludge is mixed with carbon black or oil carbon before neutralization.

15. The method of claim 10, wherein said anionic surfactant is selected from fatty acid-type surfactants, naphthenic acid-type surfactants, sulfonic acid-type surfactants and sulfate-type surfactants.

16. The method of claim 10, wherein said anionic surfactant is added after washing said acid sludge with water.

17. The method of claim 10, wherein said polyvalent inorganic salt is a water soluble aluminum salt.

* * * * *